United States Patent
Qian

(10) Patent No.: US 8,609,741 B2
(45) Date of Patent: *Dec. 17, 2013

(54) DENTAL ADHESIVE AND METHOD OF USE

(71) Applicant: Kerr Corporation, Orange, CA (US)

(72) Inventor: Xuejun Qian, Foothill Ranch, CA (US)

(73) Assignee: Kerr Corporation, Orange, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/658,954

(22) Filed: Oct. 24, 2012

(65) Prior Publication Data

US 2013/0045465 A1    Feb. 21, 2013

Related U.S. Application Data

(63) Continuation of application No. 13/164,537, filed on Jun. 20, 2011, now Pat. No. 8,297,976, which is a continuation of application No. 11/868,748, filed on Oct. 8, 2007, now Pat. No. 7,963,769.

(51) Int. Cl.
| | |
|---|---|
| *A61L 2/08* | (2006.01) |
| *B29C 71/04* | (2006.01) |
| *C08F 2/46* | (2006.01) |
| *C08G 61/04* | (2006.01) |

(52) U.S. Cl.
USPC ............. 522/79; 522/74; 522/71; 522/189; 522/1; 520/1

(58) Field of Classification Search
USPC .................. 522/79, 74, 71, 189, 1; 520/1
See application file for complete search history.

(56) References Cited

U.S. PATENT DOCUMENTS

| | | | |
|---|---|---|---|
| 4,567,030 A | 1/1986 | Yuasa et al. | |
| 4,775,585 A | 10/1988 | Hagiwara et al. | |
| 4,792,632 A | 12/1988 | Ellrich et al. | |
| 4,911,899 A | 3/1990 | Hagiwara et al. | |
| 5,609,675 A | 3/1997 | Noritake et al. | |
| 5,658,963 A | 8/1997 | Qian et al. | |
| 6,288,138 B1 | 9/2001 | Yamamoto et al. | |
| 6,355,704 B1 | 3/2002 | Nakatsuka et al. | |
| 6,790,877 B2 * | 9/2004 | Nakatsuka et al. | ........... 523/118 |
| 6,900,251 B2 | 5/2005 | Moszner et al. | |
| 6,902,608 B2 | 6/2005 | Erdmann et al. | |
| 6,994,551 B2 | 2/2006 | Wang et al. | |
| 7,226,960 B2 | 6/2007 | Jia | |
| 7,963,769 B2 * | 6/2011 | Qian | ................. 433/228.1 |
| 2004/0229973 A1 | 11/2004 | Sang et al. | |
| 2006/0084717 A1 * | 4/2006 | Cohen et al. | ................ 523/116 |
| 2007/0155853 A1 * | 7/2007 | Chen et al. | ................ 523/109 |

FOREIGN PATENT DOCUMENTS

| | | |
|---|---|---|
| WO | 03013444 A1 | 2/2003 |
| WO | 03035013 A1 | 5/2003 |
| WO | 03051316 A1 | 6/2003 |
| WO | 2004071470 A1 | 8/2004 |

\* cited by examiner

*Primary Examiner* — Ling Choi
*Assistant Examiner* — Jessica E Whiteley
(74) *Attorney, Agent, or Firm* — Wood, Herron & Evans, LLP

(57) ABSTRACT

A dental adhesive composition comprising (i) at least one non-acidic polymerizable monomer having at least one ethylenically unsaturated group, (ii) optionally one or more acidic compounds, (iii) at least one photoinitiator, (iv) at least one solvent, and (v) about 0-40% by weight of one or more fillers; wherein the weight ratio of non-acidic polymerizable monomers/acidic compounds in the adhesive composition is more than about 4.5; the viscosity of the adhesive composition is less than about 350 centipoise (cP) at 25° C.; and the adhesive composition excluding solvent and filler has an acid number of less than about 0.75 mmol NaOH/g. The dental adhesive composition is used with a dental primer composition, which may be provided together in a kit.

20 Claims, No Drawings

000

DENTAL ADHESIVE AND METHOD OF USE

RELATED APPLICATION

This application is a continuation of co-pending U.S. application Ser. No. 13/164,537 filed on Jun. 20, 2011, which is a continuation of U.S. patent application Ser. No. 11/868,748 filed Oct. 8, 2007 and issued on Jun. 21, 2011 as U.S. Pat. No. 7,963,769, the disclosures of which are incorporated herein by reference in their entirety.

TECHNICAL FIELD

A dental adhesive composition, a kit containing the adhesive composition, and a method of using the adhesive composition that results in a low film thickness, improved compatibility with self-cured resin cement/composite resin, and enhanced enamel bond strength.

BACKGROUND

Currently available dental adhesive systems for bonding to a dental substrate for various restorative procedures can be classified into two major classes.

The first class is referred to as a total-etch adhesive system. It requires use of an acid etchant, usually a phosphoric acid, to remove the smear layer covering the tooth structure and to demineralize the tooth structure (tooth structure can be either dentin or enamel) so that the primer and adhesive can effectively penetrate into the tooth structure, forming a hybrid layer for enhanced adhesion. A total-etch adhesive system requires a separate acid etchant to etch the tooth structure, and must be rinsed before primer/adhesive application. Because the acid etchant is quite acidic, contact with soft tissue may cause patient irritation or discomfort. The acid etchant removes the smear layer and exposes the dentinal tubules so, if not completely sealed with a primer/adhesive, the open tubules cause sensitivity or discomfort under external stimuli (cold, pressure, etc.) as a result of hydrodynamic fluid movement inside dentinal tubules.

The second class of dental adhesive systems is referred to as a self-etch adhesive system. It eliminates the drawbacks associated with the total-etch adhesive system. That is, a self-etch adhesive system does not require a separate acid etchant, and the self-etch primer/adhesive is not rinsed off so there is less chance of a strongly acidic compound in contact with soft tissues. In the self-etch adhesive system, the primer/adhesive penetrates to and seals wherever it etches, so dentinal tubules are not opened and exposed. With the self-etch adhesive system, there is less technique sensitivity because there is no need to maintain a certain wetness of the dentin surface before applying the adhesive.

The self-etch adhesive system has two subclasses. The first sub-class consists of a self-etch primer and an adhesive, applied sequentially to a tooth structure. The second sub-class combines an etchant, a primer, and an adhesive to form a single-component self-etch priming adhesive system.

While current self-etch adhesive systems bond well to a dentin structure, their bond strength to an enamel structure, especially un-cut enamel, is often inadequate and significantly lower than bond strengths obtained with a total-etch adhesive system counterpart. There is thus a need for a self-etch system that provides improved adhesion to an enamel structure.

Current light-curable dental adhesives, both total-etch and self-etch types, do not work well with self-cured resin cements for indirect applications, especially when cementing a metal-based inlay, onlay, crown, or post. They also do not work well with self-cured composite resins (filling material or core buildup material). One reason is that some systems use an adhesive that does not contain a solvent and thus has a high viscosity, which results in a rather thick adhesive film. A thick adhesive film may interfere with seating an indirect restoration (inlay, onlay, or crown), whereas a thick adhesive film is fine with a direct composite restoration where a composite resin is placed over the adhesive film to fill the cavity and then light-cured. Another reason current light-curable dental adhesives do not work well with self-cured composite resins is that some adhesives contain a high concentration of acidic monomers and therefore are quite acidic, resulting in poor compatibility with a self-curing composite resin (filling material or core buildup material) or a resin cement for indirect restorations, especially when cementing metal-based indirect restoration in which light-curing is limited. The redox initiator system used in most self-cure or dual-cure resin cements or composite resins contains a benzoyl peroxide (BPO) catalyst and a tertiary amine activator. Upon light-curing, the adhesive has a superficial oxygen-inhibited layer containing un-cured acidic monomers. If the adhesive is too acidic, the acid within the oxygen inhibited layer can neutralize the tertiary amine of the resin cement or composite resin coming in contact with the adhesive, thus retarding or preventing the self-curing reaction of the resin cement or composite resin, and resulting in weak adhesion between the self-cured resin cement or composite resin and the acidic adhesive. Another reason current light-curable dental adhesives do not work well clinically is that most self-etching adhesives yield inadequate bond strength to an un-cut enamel structure due to poor etching efficacy of the self-etching primer or adhesive.

Some adhesive systems introduce an additional self-cure activator to improve compatibility between the acidic adhesive and the self-cured resin cement/composite resin. While the efficacy of the self-cure activator is debatable, use of an additional self-cure activator introduces complexity and inconsistency into restorative procedures, e.g., the activator must be mixed with the adhesive prior to application and the adhesive/activator ratio will vary from one application to the next.

Improved dental adhesives are thus desirable.

DETAILED DESCRIPTION

A light-curable dental adhesive composition and kit comprising the adhesive composition for use in restorative dentistry, endodontic, and/or orthodontic applications are disclosed. The disclosed composition yields a thin adhesive layer so that it does not interfere with seating indirect restorations. The disclosed composition has an acidity that is compatible with current resin cements or composite resins that employ a BPO/tertiary amine redox initiator system or other redox initiator systems. The disclosed composition yields excellent adhesion when the resin cement or composite resin is self-cured, without the need for an activator. The disclosed adhesive kit yields improved bond strength to enamel.

The disclosed light-curable dental adhesive composition, when used with a primer, resolves shortcomings associated with current dental adhesives. When the dental adhesive is used with a primer or with a priming adhesive (which combines the ingredients of the primer and the adhesive into a single composition), upon application, drying, and light-curing, the cured dental adhesive has a low film thickness (less than 30 microns). Thus, it does not interfere with seating of a prosthetic device such as an inlay, onlay, or crown. The acidity of the disclosed dental adhesive composition is well controlled so that it does not interfere with redox initiator systems, especially BPO/tertiary amine redox initiator systems, of current resin cement or core buildup materials. Therefore, when used with self-cured resin cement or core buildup materials, excellent bond strength can be obtained without using an additional self-cure activator. The disclosed dental adhesive composition can be used with any acidic dental primer or priming adhesive, either a total-etch system or a self-etch system, to make them suitable with both direct and indirect applications as a result of reduced film thickness and acidity. The disclosed dental adhesive composition results in good curing and is well suited as a desensitizer to reduce or eliminate tooth sensitivity.

One embodiment is a kit comprising a primer (a total-etch primer or self-etch primer) composition and the disclosed dental adhesive composition that yields excellent adhesion to an un-cut enamel structure, which results in a thin adhesive layer that does not interfere with seating indirect restorations, and is not too acidic and thus is compatible with a self-cured resin cement or composite resin (filling material or core buildup material), resulting in enhanced adhesion. The kit can also be used for desensitizing a hyper-sensitive tooth. A self-etch primer composition is also disclosed for use with the disclosed dental adhesive composition to achieve enhanced enamel bond strength.

Another embodiment is a method using the disclosed dental adhesive composition in combination with a primer or priming adhesive to render the primer or priming adhesive suitable for indirect applications, and compatible with any self-cured resin cement or composite resin (filling material or core buildup material) without an activator. The method uses the disclosed dental adhesive composition in combination with a primer for direct restorative procedures (with a composite filling material or core buildup material), indirect restorative procedures (with a resin cement for cementing veneers, inlays, onlays, crowns, and posts), and/or orthodontic procedures (with orthodontic cement for cementing orthodontic appliances). The method also uses the disclosed dental adhesive composition in combination with a primer, especially a self-etch primer, to desensitize the tooth.

The disclosed dental adhesive or restorative kit comprises (I) a dental primer composition; and (II) a dental adhesive composition.

The dental adhesive composition comprises:
(i) at least one non-acidic polymerizable monomer having at least one ethylenically unsaturated group,
(ii) optionally one or more acidic compounds,
(iii) at least one photoinitiator,
(iv) at least one solvent, and
(v) about 0-40% by weight of one or more fillers,
where the weight ratio of the non-acidic polymerizable monomers/acidic compounds is more than about 4.5; the viscosity of the composition is less than about 350 centipoise (cP) at 25° C.; and the composition excluding solvent and filler has an acid number, subsequently defined, of less than about 0.75 mmol NaOH/g.

For component (i) of the dental adhesive composition, i.e., at least one non-acidic polymerizable monomer having at least one ethylenically unsaturated group, the non-acidic polymerizable monomer contains at least one ethylenically unsaturated group, but contains no acid moiety. Examples of ethylenically unsaturated groups include, but are not limited to, (meth)acrylate{(meth)acrylate=acrylate or methacrylate}, acrylamide, methacrylamide, and vinyl groups. Examples of non-acidic polymerizable monomers include, but are not limited to, hydroxyethyl (meth)acrylate (HEMA), hydroxypropyl(meth)acrylate, hydroxybutyl(meth)acrylate; glyceryl di(meth)acrylate (GDMA), glyceryl mono(meth)acrylate, methyl(meth)acrylate, ethyl(meth)acrylate, propyl(meth)acrylate, butyl(meth)acrylate, hexyl(meth)acrylate, octyl(meth)acrylate, lauryl(meth)acrylate, decyl(meth)acrylate, tridecyl(meth)acrylate; 2-ethoxyethyl(meth)acrylate, 2'-ethoxy-2-ethoxyethyl(meth)acrylate, ethyleneglycol di(meth)acrylate, diethyleneglycol di(meth)acrylate, triethyleneglycol di(meth)acrylate (TEGDMA), tetraethyleneglycol di(meth)acrylate, polyethyleneglycol mono-(meth)acrylate, polyethyleneglycol di-(meth)acrylate, polypropyleneglycol mono-(meth)acrylate, polypropyleneglycol di-(meth)acrylate, polytetramethyleneglycol mono-(meth)acrylate, polytetramethyleneglycol di-(meth)acrylate, hexanediol di(meth)acrylate, trimethyloylpropane tri(meth)acrylate, ethoxylated trimethyloylpropane tri(meth)acrylate (ETMPTA), UDMA (reaction product of 2-hydroxyethyl methacrylate with 2,4,4-trimethylhexane diisocyanate), 2,2-bis[4-(2-hydroxy-3-methacryloylpropoxy)-phenyl]-propane (Bis-GMA), ethoxylated bisphenol A dimethacrylate ("EB-PADMA-n", n=total number of moles of ethylene oxide in the molecule, with 2-20 units preferred), tetrahydrofurfuryl (meth)acrylate, N,N'-methylenebis(acrylamide), N,N'-ethylenebis(acrylamide), N,N'-butylenebis(acrylamide), or a mixture thereof. In one embodiment, component (i) comprises at least one polymerizable monomer having at least one hydroxyl group. Examples of hydroxyl-containing polymerizable monomers include, but are not limited to, hydroxyethyl (meth)acrylate (HEMA), hydroxypropyl(meth)acrylate, hydroxybutyl(meth)acrylate, glyceryl di(meth)acrylate (GDMA), glyceryl mono(meth)acrylate, 2,2-bis[4-(2-hydroxy-3-methacryloylpropoxy)-phenyl]-propane (Bis-GMA).

For component (ii) of the dental adhesive composition, i.e., optionally one or more acidic compounds, any acidic compound may be used. An acidic compound with any acidic moiety may be used. Examples of acidic moieties include, but are not limited to, nitric acid, sulfonic acid, sulfinic acid, carboxylic acid, carboxylic acid anhydride, phosphonic acid or its derivatives, phosphoric acid or its derivatives, with a derivative being a salt or ester of the respective acid. In one embodiment, the acidic compound is an organic acid. In one embodiment, the acidic compound is an acidic polymerizable monomer having at least one ethylenically unsaturated group and at least one acidic moiety. Examples of ethylenically unsaturated groups include, but are not limited to, acrylate, methacrylate, acrylamide, methacrylamide, and vinyl groups. The acidic moiety can be any acidic functional group. Examples of acidic moieties include, but are not limited to, sulfonic acid, sulfinic acid, carboxylic acid, carboxylic acid anhydride, phosphonic acid or its derivatives, phosphoric acid or its derivatives, with a derivative being a salt or ester of the respective acid. In one embodiment, the acidic polymerizable monomer contains at least one acidic moiety that is phosphonic acid or its derivatives, or phosphoric acid or its derivatives. Examples includes, but are not limited to, phenyl methacryloxyethyl phosphate, glyceryldimethacrylate phosphate (GDMA-P), dipentaerithritol pentaacrylate phosphate, methacryloyloxydecyl phosphate, hydroxyethylmethacrylate phosphate, and/or bis(hydroxyethylmethacrylate) phosphate. In another embodiment, the acidic monomer contains at least one acidic moiety selected from carboxylic acid and carboxylic anhydride. Examples includes, but are not limited to, maleic acid, itaconic acid, methacrylic acid, acrylic acid, polymerizable homopolymer or copolymer of an α, β-unsaturated carboxylic acid such as (meth)acrylated poly(acrylic acid), (meth)acrylated poly(acrylic acid)copolymer such as (meth)acrylated poly(acrylic acid-maleic acid)copolymer or (meth)acrylated poly(acrylic acid-maleic acid-itaconic acid) copolymer, maleic anhydride, 4-methacryloxyethyltrimellitic anhydride, 4-methacryloxyethyltrimellitic acid, any addition product of mono- or di-anhydride compound with an hydroxyalkylmethacrylate compound such as the addition product of pyromellitic acid anhydride and 2-hydroxyethyl methacrylate, the addition product of pyromellitic acid anhydride and glyceryl dimethacrylate, the addition product of 3,3',4,4'-benzophenonetetracarboxylic dianhydride and hydroxyethyl methacrylate, the addition product of phthalic anhydride and hydroxyethyl methacrylate, the addition product of maleic anhydride and glyceryl dimethacrylate, and combinations of these.

In one embodiment, the dental adhesive composition comprises at least one acidic compound (ii) and the weight ratio of non-acidic polymerizable monomers/acidic compounds is more than about 4.5. In one embodiment, the weight ratio of non-acidic polymerizable monomers/acidic compounds is more than about 6.0. In one embodiment, the weight ratio of non-acidic polymerizable monomers/acidic compounds is more than about 8.0. In one embodiment, the weight ratio of non-acidic polymerizable monomers/acidic compounds is more than about 10.0.

The acidity of the dental adhesive composition may be controlled by careful selection of both the type of acidic compound(s) and the concentration of the acidic compound (s), so that the adhesive dental composition, excluding solvent and filler, has an acid number, subsequently defined, of less than about 0.75 mmol NaOH/gram. In one embodiment, dental adhesive composition, excluding solvent and filler, has an acid number less than about 0.6 mmol NaOH/gram. In another embodiment, the dental adhesive composition, excluding solvent and filler, has an acid number less than about 0.5 mmol NaOH/gram. In one embodiment, the dental adhesive composition, excluding solvent and filler, has an acid number ranging from about 0.001 mmol NaOH/gram to about 0.75 mmol NaOH/gram. In another embodiment, the dental adhesive composition, excluding solvent and filler, has an acid number ranging from about 0.1 mmol NaOH/gram to about 0.6 mmol NaOH/gram. In yet another embodiment, the dental adhesive composition, excluding solvent and filler, has an acid number ranging from about 0.2 mmol NaOH/gram to about 0.5 mmol NaOH/gram. The acid number of a composition is determined by a titration method whereby a certain amount of the acidic composition is first dissolved in 85% isopropanol aqueous solution and titrated with NaOH solution (e.g., 0.1N NaOH solution) until the solution pH reaches 7.0. The amount (mmol) of NaOH needed to titrate one gram of a composition is defined as its acid number (mmol NaOH/gram).

In one embodiment, the dental adhesive composition comprises no acidic compound (ii).

For component (iii) of the dental adhesive composition, i.e., a photoinitiator, the photoinitiator may be any compound that generates free radicals upon exposure to a light source and causes polymerization or hardening of the composition. The light source can be any dental curing light that emits light in the visible or ultraviolet range. Examples of photoinitiators include, but are not limited to, benzoin, benzoin ethers and esters, 2,2-diethoxy acetophenone, diketone compounds such as camphorquinone (CQ) and 1-phenyl-1,2-propanedione, monoacylphosphine oxide, bisacylphosphine oxide as disclosed in U.S. Pat. No. 4,792,632, which is expressly incorporated by reference herein in its entirety, diaryliodonium salt, triarylsulfonium salt, and a mixture of photoinitiators. In one embodiment, a coinitiator may be used with a photoinitiator to enhance curing efficiency. Coinitiators include tertiary amine and sulfinate compounds. Examples of coinitiators include, but are not limited to, ethyl 4-(N,N-dimethylamino)benzoate (EDMAB), 4-(N,N-dimethylamino)benzoic acid, 4-(N,N-dimethylamino) benzonitrile, 4-(N,N-dimethylamino)benzaldehyde, 2-(ethylhexyl)-4-(N,N-dimethylamino)benzoate (ODMAB), N,N-dimethylaminoethyl methacrylate, N,N-dimethylaminophenethyl alcohol, sodium benzenesulfinate, and sodium toluenesulfinate. In one embodiment, a photoinitiator system includes the combination of camphorquinone and a tertiary amine Examples of tertiary amines include, but are not limited to, ethyl 4-(N,N-dimethylamino)benzoate, 4-(N,N-dimethylamino)benzoic acid, 4-(N,N-dimethylamino)benzonitrile, 4-(N,N-dimethylamino)benzaldehyde, 2-(ethylhexyl)-4-(N,N-dimethylamino)benzoate, N,N-dimethylaminoethyl methacrylate, N,N-dimethylaminophenethyl alcohol. In one embodiment, a photoinitiator system includes the combination of camphorquinone and bisacylphosphine oxide or monoacylphosphine oxide. In one embodiment, a photoinitiator is present at a concentration of about 0.01% (w/w) to about 10% (w/w) of the total weight of the dental adhesive composition. In another embodiment, a photoinitiator is present at a concentration of about 0.05% (w/w) to about 5% (w/w) of the total weight of the dental adhesive composition.

For component (iv) of the dental adhesive composition, i.e., a solvent, any solvent may be used. The solvent reduces the viscosity of the adhesive composition so that when applied to a dental structure (a dental structure includes dentin, enamel, and a prosthetic device such as an inlay, an onlay, or a crown), the composition will readily thin or spread itself out, resulting in a thin adhesive layer thickness. A thin adhesive layer (less than about 40 microns) is desirable so that the cured composition does not interfere with seating of a prosthetic device such as an inlay, onlay, veneer, crown, or post. In one embodiment, the solvent has a low viscosity so that the resulting composition has a low viscosity. In another embodiment, the solvent has a boiling temperature less than about 110° C. so that the solvent can be easily removed from the dental adhesive composition using compressed air from a dental syringe. In one embodiment, the solvent may be ethanol, water, methanol, acetone, methyl ethyl ketone, isopropanol, and/or t-butanol. In one embodiment, the solvent may be ethanol, methanol, acetone, methyl ethyl ketone, isopropanol, and/or t-butanol. In one embodiment, the concentration of the solvent is between about 1% by weight and about 85% by weight of the total dental adhesive composition. In another embodiment, the concentration of solvent is between about 5% by weight and about 70% by weight of the total dental adhesive composition. In yet another embodiment, the concentration of solvent is between about 15% by weight and about 60% by weight of the total dental adhesive composition. In one embodiment, the viscosity of the adhesive dental composition is less than about 350 centipoise (cP) at 25° C. In another embodiment, the viscosity of the adhesive dental composition is less than about 250 centipoise (cP) at 25° C. In yet another embodiment, the viscosity of the adhesive dental composition is less than about 150 centipoise (cP) at 25° C. In yet another embodiment, the viscosity of the dental adhesive composition is less than about 100 centipoise (cP) at 25° C. The viscosity (in centipoise or cP) of the composition is measured at 25° C. with a Brookfield Viscometer (Model RVT, Brookfield Engineering Laboratories Inc., MA) using a 15 ml sample chamber and Cylindrical Spindle No. 21 operated at a speed of 50 rpm.

For component (v) of the dental adhesive composition, i.e., about 0-40% by weight of one or more fillers, the one or more fillers can be optionally incorporated into the adhesive composition. Examples of fillers include, but are not limited to, inorganic metal, salt, oxide, fluoride, nitride, silicate glass, aluminosilicate glass, aluminoborosilicate glass, fluoroaluminosilicate glass, quartz, colloidal silica, precipitated silica, zirconia-silica, polymeric filler, and/or polymerized composite fillers with inorganic particles. In one embodiment, inorganic fillers for increased x-ray contrast ability include metals, salts, oxides, fluorides, silicate glass, aluminosilicate glass, aluminoborosilicate glass, and fluoroaluminosilicate glass containing elements of high atomic number such as Sr, Y, Zr, Ba, La, Hf, Zn, Bi, W, rare earth metals, and combinations of these. Examples include barium sulfate, silver, strontium fluoride, barium fluoride, ytterbium fluoride, yttrium fluoride, barium tungstate, zinc oxide, bismuth(III) oxide, barium aluminosilicate, barium aluminoborosilicate, strontium aluminosilicate, barium fluoroaluminosilicate, strontium fluoroaluminosilicate, strontium zinc fluoroaluminosilicate, zinc aluminosilicate, etc. Fumed silica, colloidal silica, or precipitated silica can also be incorporated to improve the dispersion of the filler, as well as the rheological and handling properties of the composition. Examples of colloidal silicas are Aerosil® series such as OX-50, OX-130, and OX-200 silica (Degussa, Ridgefield Park N.J.), and Cab-O-Sil® M5 and Cab-O-Sil® TS-530 silica (Cabot Corp., Tuscola Ill.). The filler also includes nanoparticles such as those obtained through a sol-gel process. Examples include those disclosed in U.S. Pat. Nos. 4,567,030 and 5,609,675, each expressly incorporated by reference herein in its entirety. Mixtures of different fillers can be used. For inorganic fillers, the surface of the filler may be treated or coated with a coupling agent, such as gamma-methacryloyloxypropyltrimethoxy-silane (MPTMS), that enhances the interfacial bonding between the filler and resin matrix and improves mechanical properties. In one embodiment, the mean particle size of the filler is less than about 50 microns. In another embodiment, the mean particle size of the filler is less than about 10 microns. In yet another embodiment, the mean particle size of the filler is less than about 5 microns. The concentration of total filler(s) ranges from about 0% (w/w) to about 40% (w/w) of the total dental adhesive composition. In one embodiment, the concentration of total filler(s) ranges from about 0% (w/w) to about 25% (w/w) of the total dental adhesive composition. In another embodiment, the concentration of total filler(s) ranges from about 5% (w/w) to about 25% (w/w) of the total dental adhesive composition. In yet another embodiment, the concentration of total filler(s) is at least about 1% (w/w), and up to about 40% (w/w).

Other ingredients can also be incorporated in the dental adhesive composition, such as a colorant, a stabilizer, a UV absorber, a fluoride-releasing compound, and/or an antimicrobial additive. A colorant may be used to achieve a desired color or shade and can be an inorganic pigment and/or an organic dye. A stabilizer is a polymerization inhibitor or retarder to improve the shelf stability of the dental adhesive composition. Most commonly used stabilizers include 2,6-di-(tert-butyl)-4-methylphenol (butylated hydroxytoluene or "BHT") and 4-methoxyphenol (monomethyl ether hydroquinone or "MEHQ"). A UV absorber may be used to improve the color stability of the adhesive composition upon exposure to UV light. An example of UV absorber is 2-hydroxy-4-methoxybenzophenone ("UV-9"). A fluoride-releasing compound is any fluoride-containing substance that can release fluoride into saliva, water, or surrounding dentition. Examples of fluoride-releasing compounds include, but are not limited to, sodium fluoride, strontium fluoride, sodium hexafluorosilicate, zinc hexafluorosilicate, rare earth metal fluoride such as ytterbium fluoride, a salt formed by an amine and hydrofluoric acid, and/or a complex formed by an amine and $BF_3$. An antimicrobial additive may be used to impart antimicrobial effects to the composition. Examples of antimicrobial additives include, but are not limited to, benzalkonium chloride, iodoform, eugenol, zinc oxide, triclosan, alkyl 4-hydroxybenzoate, silicate glass powder containing silver and/or zinc, and zeolite powder containing silver and/or zinc ion(s). Antibacterial zeolites and their preparation are disclosed in U.S. Pat. Nos. 4,911,899 and 4,775,585, each of which is expressly incorporated by reference herein in its entirety.

The dental primer composition (I) in the adhesive or restorative kit can be a total-etch primer composition or a self-etch primer composition. In one embodiment, the primer composition is a commercial total-etch primer such as OptiBond™ Prime (Kerr Corp. Orange Calif.). In one embodiment, the primer composition is a commercial self-etch primer. In one embodiment, the primer composition is a commercial total-etch priming adhesive or a commercial self-etch priming adhesive. An example of a commercial total-etch priming adhesive is Prime & Bond® NT (Dentsply, Pa.). An example of a commercial self-etch priming adhesive is OptiBond™ All-In-One (Kerr Corp., Orange Calif.).

The primer composition (I) comprises at least one solvent, and at least one acidic polymerizable monomer having at least one ethylenically unsaturated group and at least one acidic moiety. Examples of ethylenically unsaturated groups include, but are not limited to, acrylate, methacrylate, acrylamide, methacrylamide, and vinyl groups. In one embodiment, the acidic monomer contains at least one acidic moiety selected from carboxylic acid or carboxylic anhydride. Examples includes, but are not limited to, maleic acid, itaconic acid, methacrylic acid, acrylic acid, polymerizable homopolymer or copolymer of an α, β-unsaturated carboxylic acid such as (meth)acrylated poly(acrylic acid), (meth)acrylated poly(acrylic acid)copolymer such as (meth)acrylated poly(acrylic acid-maleic acid)copolymer or (meth)acrylated poly(acrylic acid-maleic acid-itaconic acid) copolymer, maleic anhydride, 4-methacryloxyethyltrimellitic anhydride, 4-methacryloxyethyltrimellitic acid, any addition product of mono- or dianhydride compound with a hydroxyalkylmethacrylate compound such as the addition product of pyromellitic acid anhydride and 2-hydroxyethyl methacrylate, the addition product of pyromellitic acid anhydride and glyceryl dimethacrylate, the addition product of 3,3',4,4'-benzophenonetetracarboxylic dianhydride and hydroxyethyl methacrylate, the addition product of phthalic anhydride and hydroxyethyl methacrylate, the addition product of maleic anhydride and glyceryl dimethacrylate, and combinations of these. In one embodiment, the acidic monomer is selected from 4-methacryloxyethyltrimellitic anhydride or 4-methacryloxyethyltrimellitic acid.

In one embodiment, the acidic monomer contains at least one acidic moiety selected from phosphonic acid or its derivatives or phosphoric acid or its derivatives, with a derivative being a salt or ester of the respective acid. Examples include, but are not limited to, phenyl methacryloxyethyl phosphate, glyceryldimethacrylate phosphate, dipentaerithritol pentaacrylate phosphate, methacryloyloxydecyl phosphate, hydroxyethylmethacrylate phosphate, and/or bis(hydroxyethylmethacrylate)phosphate.

Other acidic monomers may also be incorporated. However, acidic monomers containing sulfonic acid moiety is less preferred. In one embodiment, the primer composition is substantially free from acidic monomers containing sulfonic acid moiety.

The solvent in the primer composition (I) can be any solvent. In one embodiment, the solvent has a boiling temperature less than about 110° C. so that the solvent can be easily removed from the dental adhesive composition using compressed air from a dental syringe. In one embodiment, the solvent in the primer composition is selected from water, ethanol, methanol, acetone, methyl ethyl ketone, isopropanol, and/or t-butanol. In another embodiment, the solvent includes the combination of water and at least one of ethanol, methanol, acetone, methyl ethyl ketone, isopropanol, and/or t-butanol.

In one embodiment, the primer composition (I) further comprises one or more components selected from a non-acidic polymerizable monomer having at least one ethylenically unsaturated group, a polymerization initiator, a filler, a stabilizer, a fluoride-releasing compound, and/or an antimicrobial additive. The optional non-acidic polymerizable monomer in the primer composition has the same meaning, selections, and embodiments as the non-acidic polymerizable monomer of component (i) of the adhesive composition (II) disclosed fully in previous sections. In one embodiment, the non-acidic polymerizable monomer is a monomer having at least one hydroxyl group. The optional filler in the primer composition has the same meaning, selections, and embodiments as the filler component (v) of the adhesive composition (II) disclosed fully in previous sections. The optional stabilizer, fluoride-releasing compound, and antimicrobial additive in the primer composition have the same meanings, selections, and embodiments as those of the adhesive composition (II) disclosed in previous sections. The optional polymerization initiator is selected from at least part of a photoinitiator system, at least part of a redox initiator system, and/or a sulfinate salt. The examples of photoinitiators are the same as those for the photoinitiator component (iii) of the adhesive composition (II). In one embodiment, the photoinitiator is selected from camphorquinone, bisacylphosphine oxide, and/or monoacylphosphine oxide.

In one embodiment, the primer composition (I) comprises about 1% w/w to about 50% w/w of at least one acidic polymerizable monomer having at least one acidic group selected from phosphonic acid or its derivatives or phosphoric acid or its derivatives; about 0 to about 60% w/w of one or more non-acidic polymerizable monomers; about 1% w/w to about 50% w/w water; about 0-70% w/w of one or more organic solvents selected from ethanol, acetone, methyl ethyl ketone, isopropanol, and/or t-butanol; and optionally one or more components selected from a polymerization initiator, a filler, a stabilizer, a fluoride-releasing compound, and/or an antimicrobial additive.

In one embodiment, the primer composition (I) comprises about 5% w/w to about 35% w/w of at least one acidic polymerizable monomer having at least one acidic group selected from phosphonic acid or its derivatives or phosphoric acid or its derivatives; about 1% w/w to about 40% w/w of at least one non-acidic polymerizable monomer; about 5% w/w to about 35% w/w of water; about 10% w/w to about 60% w/w of at least one organic solvent selected from ethanol, acetone, methyl ethyl ketone, isopropanol, and/or t-butanol; and optionally one or more components selected from a polymerization initiator, a filler, a stabilizer, a fluoride-releasing compound, and/or an antimicrobial additive.

In one embodiment, the primer composition (I) comprises about 5% w/w to about 35% w/w of at least one acidic polymerizable monomer containing phosphoric acid or its derivatives; about 1% w/w to about 40% w/w of at least one non-acidic polymerizable monomer comprising at least one hydroxyl-containing monomer; about 5% w/w to about 35% w/w water; about 10% w/w/to about 60% w/w of at least one organic solvent selected from ethanol and/or acetone; and optionally one or more components selected from a polymerization initiator, a filler, a stabilizer, a fluoride-releasing compound, and/or an antimicrobial additive.

The adhesive composition (II) in the adhesive or restorative kit is a light-curable single-part system with all ingredients combined. According to embodiments, the adhesive composition (II) may be packaged in a plastic bottle, in a syringe, or in a single-dose container. The primer composition (I) in the adhesive or restorative kit is a single-part system with all ingredients combined. According to embodiments, the primer composition (I) may be packaged in a plastic bottle, in a syringe, or in a single-dose container. The adhesive or restorative kit may also include instructions for use. In one embodiment, the primer composition (I) and the adhesive composition (II) in the adhesive or restorative kit are packaged in a dual-chamber container or device with the primer composition in the first chamber and the adhesive composition in the second chamber. The dual-chamber container or device can be a single-dose or multi-dose container or device.

In one embodiment, the kit also contains at least one of an acidic etchant for dentin/enamel, an acidic etchant for ceramics, a silane primer, a metal primer, a composite resin, a resin cement, and/or a pit/fissure sealant. The acidic etchant for dentin/enamel is used to etch the tooth structure (dentin or enamel) to enhance adhesion. The acidic etchant for ceramics is used to etch the ceramic (including porcelain) or composite substrate of a prosthetic device to enhance its adhesion. The acidic etchant composition comprises at least one acid selected from phosphoric acid, maleic acid, citric acid, and/or hydrofluoric acid. A silane primer is used to prime the ceramic or composite substrate of a prosthetic device to enhance adhesion. A metal primer is be used to prime the metallic substrate (e.g., metal alloy, zirconia, or alumina) of a prosthetic device to enhance adhesion. A composite resin is selected from a composite resin filling material or a core buildup material. The curing mechanism for a composite resin is light-cure only, self-cure only, or dual-cure (i.e., the combination of light-cure and self-cure). A composite resin filling material is used to fill the dental cavity and restore tooth function. An example of a commercial composite resin filling material is Premise™ (Kerr Corp.), a light-curable restorative filling material. A composite resin filling material also includes light-cure flowable composite resins such as Premise™ Flowable (Kerr Corp.) and self-cure composite resins such as BISFIL™ II (Bisco IL). A core buildup material is used to build up missing tooth structure to receive a crown. A core buildup material can be a light-cure only, a self-cure only, or a dual-cure core buildup material. An example of dual-cure composite resin core buildup material is CoreRestore™ 2. Core buildup materials can also include resin-modified materials such as Vitremer™ Core Buildup (3M ESPE, MN) material. A resin cement is used to attach or adhere a prosthetic or orthodontic device to tooth structure. Examples of prosthetic or orthodontic devices include a veneer, an inlay, an onlay, a crown, a post, an orthodontic bracket, or an orthodontic band. A resin cement can be a light-cure only, a self-cure only, or a dual-cure resin cement. An example of a dual-cure resin cement is Nexus™ 2 resin cement (Kerr Corp., CA). An example of a resin cement for adhering an orthodontic device to tooth structure is Transbond XT™ Light-Cure Adhesive (3M Unitek, MN) (resin cement is often termed "adhesive" in the orthodontic community). Significantly enhanced adhesion results when the disclosed adhesive dental composition is used with a self-cure resin cement/core buildup material or a dual-cure resin cement/core buildup material when there is limited or no light accessibility (e.g. when building the core in bulk or when cementing metal-based restorations), due to enhanced compatibility between the adhesive composition and self-cured resin cement/core buildup material.

The above described dental adhesive or restorative kit can be used for restorative, orthodontic, and/or endodontic applications.

In one embodiment, the dental adhesive kit is used by (1) applying the primer composition to the tooth structure; subsequently, (2) applying the adhesive composition to the tooth structure; and (3) hardening the adhesive composition by light-curing the adhesive composition. The tooth structure can be dentin or enamel. In one embodiment, the applied primer composition is air dried using e.g., compressed air to remove volatile solvents before applying the adhesive composition. In one embodiment, the applied adhesive composition is air dried using e.g., compressed air to remove volatile solvents before light curing the adhesive composition.

In one embodiment, the tooth structure was prepared (i.e. cutting and cleaning) and optionally etched with an acidic etchant prior to applying the primer composition. In another embodiment, the primer composition is a self-etch primer and the tooth structure is not etched with an acidic etchant. In yet another embodiment, the primer composition is a total-etch primer and the tooth structure is etched with an acidic etchant prior to applying the primer composition.

In one embodiment, following light-curing of the adhesive, a composite resin or a pit/fissure sealant is applied to the adhesive-covered tooth structure and hardened. The composite resin may be a composite resin filling material or a composite resin core buildup material. The composite resin or pit/fissure sealant can be hardened by light-curing only, self-curing only, or dual-curing (i.e. the combination of self-curing and light-curing).

In one embodiment, following light-curing of the adhesive, a prosthetic or orthodontic device is attached or adhered to the adhesive-covered tooth structure with a resin cement, and then the resin cement is hardened. The prosthetic or orthodontic device may be an inlay, an onlay, a veneer, a post, a crown, an orthodontic bracket, and/or an orthodontic band. The resin cement can be hardened by light-curing only, self-curing only, or dual-curing. When cementing a veneer, light-curing the adhesive composition before cementing the veneer with a resin cement is optional, and light-curing can be performed for both the adhesive and the cement after the veneer is seated.

In one embodiment, the dental adhesive or restorative kit is used to minimize or eliminate the sensitivity of the tooth.

When the disclosed dental adhesive composition is used to bond to tooth structure, good bond strength is obtained regardless of whether the resin cement or composite resin is self-cured, light-cured, or dual-cured. In one embodiment, a bond strength≥about 15 MPa is achieved on both dentin and enamel with the disclosed dental adhesive or restorative kit. In one embodiment, a bond strength≥about 20 MPa is achieved on both dentin and enamel with the disclosed dental adhesive or restorative kit. In one embodiment, a bond strength≥about 25 MPa is achieved on both dentin and enamel with the disclosed dental adhesive or restorative kit.

The dental adhesive or restorative kit can also be used for priming the surface of a prosthetic or orthodontic device with the dental primer and/or adhesive. In one embodiment, the surface of a prosthetic or orthodontic device is treated with the disclosed dental primer and/or adhesive. The prosthetic or orthodontic device may be an inlay, an onlay, a veneer, a post, a crown, an orthodontic bracket, and/or an orthodontic band.

The current invention also discloses a method for using a dental adhesive composition in combination with a dental primer (including a dental priming adhesive) composition, where the adhesive composition and the primer composition do not have to be in the same kit. The method comprises the steps of: (1) applying a primer composition to the tooth structure; subsequently, (2) applying an adhesive composition to the tooth structure; and (3) hardening the adhesive composition by light-curing the adhesive composition. The adhesive composition comprising components (i)-(v) along with the optional components is exactly the same as the adhesive composition of the disclosed dental adhesive or restorative kit disclosed in previous sections and its disclosure/embodiments will be referenced here in its entirety whenever the adhesive composition is described in this method. The primer composition is exactly the same as the primer composition of the inventive adhesive kit disclosed in previous sections and its disclosure/embodiments will be referenced here in its entirety whenever the primer composition is described in this method. The tooth structure can be dentin or enamel.

In one embodiment, the method further comprises the steps of preparing the tooth structure (i.e. cutting and cleaning), and optionally etching the tooth structure with an acidic etchant prior to applying the primer composition. In one embodiment, the primer composition is a self-etch primer and the tooth structure is not etched with an acidic etchant. In another embodiment, the primer composition is a total-etch primer and the tooth structure is etched with an acidic etchant prior to applying the primer composition.

The primer composition can be a commercial primer or commercial priming adhesive. In one embodiment, the primer composition is a commercial total-etch primer such as OptiBond™ Prime (Kerr Corp.). In one embodiment, the primer composition is a commercial self-etch primer. In one embodiment, the primer composition is a commercial total-etch priming adhesive such as Prime & Bond® NT (Dentsply, Pa.). In one embodiment, the primer composition is a commercial self-etch priming adhesive such as OptiBond™ All-In-One (Kerr Corp.).

In one embodiment, the method further comprises the steps of air-drying the primer composition using, e.g., compressed air to remove volatile solvent before applying the adhesive composition. In one embodiment, the method further comprises the steps of air-drying the adhesive composition using e.g., compressed air to remove volatile solvents before light curing the adhesive composition.

The inventive method can be a restorative method, an orthodontic method, and/or an endodontic method.

In one embodiment, following the light-curing of the adhesive, the method further comprises the steps of applying a composite resin or a pit/fissure sealant to the adhesive-covered tooth structure and hardening the composite resin or pit/fissure sealant. The composite resin is selected from a composite resin filling material and/or a composite resin core buildup material. The composite resin or pit/fissure sealant can be hardened by light-curing only, self-curing only, or dual-curing (i.e. the combination of self-curing and light-curing).

In one embodiment, following light-curing of the adhesive, a prosthetic or orthodontic device is attached or adhered to the adhesive-covered tooth structure with a resin cement, and the resin cement is hardened. The prosthetic or orthodontic device is selected from an inlay, an onlay, a veneer, a post, a crown, an orthodontic bracket, and/or an orthodontic band. The resin cement can be hardened by light-curing only, self-curing only, or dual-curing. When cementing a veneer, the step of light-curing the adhesive composition before cementing the veneer with a resin cement is optional, and light-curing can be carried out for both the adhesive and the cement after the veneer is seated.

In one embodiment, the inventive method is used to minimize or eliminate tooth sensitivity.

The method results in good bond strength to dentin and enamel, regardless of whether the resin cement or composite resin is self-cured, light-cured, or dual-cured. In one embodiment using the method, a bond strength≥about 15 MPa is achieved on both dentin and enamel with self-cured, light-cured, or dual-cured resin cement/composite resin. In one embodiment using the method, a bond strength≥about 20 MPa is achieved on both dentin and enamel with self-cured, light-cured, or dual-cured resin cement/composite resin. In one embodiment using the method, a bond strength≥about 25 MPa is achieved on both dentin and enamel with self-cured, light-cured, or dual-cured resin cement/composite resin.

In one embodiment, the method also comprises the step of priming or treating the surface of a prosthetic or orthodontic device with a dental primer and/or adhesive. The prosthetic or orthodontic device is selected from an inlay, an onlay, a veneer, a post, a crown, an orthodontic bracket, and/or an orthodontic band.

The following Examples are illustrative and not limiting.

EXAMPLES

Abbreviations for materials used in all examples:
ST-BAS: Barium aluminoborosilicate filler that has a mean particle size of 0.4 micron and that was surface treated with γ-methacryloyloxypropyltrimethoxysilane.
Bis-GMA: 2,2-bis[4-(2-hydroxy-3-methacryloylpropoxy)-phenyl]-propane.
CQ: camphorquinone.
EDMAB: ethyl 4-(N,N-dimethylamino)benzoate.
ETMPTA: ethoxylated trimethylolpropane triacrylate with 3 moles of ethylene oxide.
GDMA: glyceryldimethacrylate.
GDMA-P: glyceryldimethacrylate phosphate.
HEMA: hydroxyethyl methacrylate.
MEHQ: 4-methoxyphenol.
ODMAB: 2-(ethylhexyl)-4-(N,N-dimethylamino)benzoate.
ST-OX-50: fumed silica OX-50 surface treated with γ-methacryloyloxypropyltrimethoxysilane.
TS-530: Surface treated fumed silica or colloidal silica sold by Cabot Corp.

A set of six specimens were used for each bond strength test.

Comparative Example 1

Adhesion to a dentin substrate was evaluated using a commercial total-etch primer OptiBond® Prime (Kerr Corp.) in combination with a commercial resin cement Nexus® 2 (Kerr Corp.). Bonding strength was evaluated as follows: The dentin surface was polished with wet 600 grit SiC paper and etched with Kerr Gel Etchant (Kerr Corp.). One coat of OptiBond® Prime was applied on the dentin surface with 15 seconds agitation, and air-dried using compressed air from a dental air syringe for about five seconds. The primer was light-cured for 20 seconds using an Optilux™ 501 (Kerr Corp.) dental curing light. A plastic mold with an inner diameter of 2.38 mm was securely placed over the primer coated dentin surface. The base and catalyst pastes of Nexus® 2 cement were mixed, condensed inside the mold, and allowed to self-cure (or dark-cure) in 37° C. water for 20-24 hours. The bond strength was tested on an Instron mechanical tester (Model 4467, Instron, MA) using shear force. A bond strength of 10.3±7.0 MPa was obtained. This low bond strength indicated an incompatibility issue between OptiBond® Prime and self-cured Nexus® 2 resin cement.

Inventive Example 1

Dental Adhesive Composition I
The following were mixed into a homogeneous adhesive composition:

| | |
|---|---|
| 4.19% w/w GDMA-P | (acidic compound) |
| 33.49% w/w Bis-GMA | (non-acidic polymerizable monomer) |
| 12.56% w/w HEMA | (non-acidic polymerizable monomer) |
| 8.37% w/w ETMPTA | (non-acidic polymerizable monomer) |
| 25.12% w/w ethanol | |
| 0.84% w/w ODMAB | |
| 0.42% w/w CQ | |
| 0.008% w/w MEHQ | |
| 5.25% w/w ST-OX-50 | |
| 1.00% w/w TS-530, and | |
| 8.75% w/w ST-BAS | |

The ratio of non-acidic polymerizable monomer/acidic compound=54.42%/4.19%=13.0. The Dental Adhesive Composition I had a viscosity of 75 cP at 25° C. The Dental Adhesive Composition I excluding filler and solvent had an acid number of 0.357 mmol NaOH/gm.

The dentin bond strength test in Comparative Example 1 was repeated using the Dental Adhesive Composition I in combination with OptiBond® Prime as follows. After applying OptiBond® Prime and air-drying, but without light-curing OptiBond® Prime, one coat of Dental Adhesive Composition I was applied to a dentin surface covered with OptiBond® Prime with 20 seconds agitation. The adhesive was then dried with compressed air from a dental air syringe for about five seconds, and polymerized by photo-curing for 20 seconds using an Optilux™ 501 (Kerr Corp.) dental curing light. A plastic mold with an inner diameter of 2.38 mm was securely placed over the adhesive coated dentin surface. The base and catalyst pastes of Nexus® 2 cement were mixed, condensed inside the mold, and allowed to self-cure (or dark-cure) in 37° C. water for 20-24 hours. The bond strength was tested on an Instron mechanical tester (Model 4467, Instron MA) using shear force. A bond strength of 31.8±4.9 MPa was obtained, which was a 209% increase over the bond strength obtained in Comparative Example 1. The high bond strength indicated improved compatibility between the inventive Dental Adhesive Composition I and self-cured Nexus® 2 resin cement.

Comparative Example 2

Adhesion to a dentin substrate was evaluated using a commercial self-etch adhesive OptiBond® All-In-One (Kerr Corp.) in combination with a commercial resin cement Nexus® 2 (Kerr Corp.). Bonding strength was evaluated as follows. The dentin surface was polished with wet 600 grit SiC paper. Two coats of OptiBond® All-In-One adhesive were applied on the dentin surface and each coat was applied with 20 seconds agitation. The adhesive was then dried with compressed air from a dental air syringe for about five seconds and polymerized by photo-curing for ten seconds using an Optilux™ 501 (Kerr Corp.) dental curing light. A plastic mold with an inner diameter of 2.38 mm was securely placed over the adhesive coated dentin surface. The base and catalyst pastes of Nexus® 2 cement were mixed, condensed inside the mold, and allowed to self-cure (or dark-cure) in 37° C. water for 20-24 hours. A bond strength of 12.5±2.7 MPa was obtained. The low bond strength indicated low compatibility between OptiBond® All-In-One adhesive and self-cured Nexus® 2 resin cement.

Inventive Example 2A

Dental Adhesive Composition II-a
The following were mixed into a homogeneous adhesive composition:

| | |
|---|---|
| 4.19% w/w GDMA-P | (acidic compound) |
| 33.49% w/w Bis-GMA | (non-acidic polymerizable monomer) |
| 12.56% w/w HEMA | (non-acidic polymerizable monomer) |
| 4.19% w/w ETMPTA | (non-acidic polymerizable monomer) |
| 4.19% w/w GDMA | (non-acidic polymerizable monomer) |
| 25.12% w/w ethanol | |
| 0.84% w/w ODMAB | |
| 0.42% w/w CQ | |
| 0.008% w/w MEHQ | |
| 5.25% w/w ST-OX-50 | |
| 1.00% w/w TS-530, and | |
| 8.75% w/w ST-BAS | |

The ratio of non-acidic polymerizable monomer/acidic compound=54.43%/4.19%=13.0. The Dental Adhesive Composition II-a had a viscosity of 75 cP at 25° C. The Dental Adhesive Composition II-a excluding filler and solvent had an acid number of 0.357 mmol NaOH/gm.

The dentin bond strength test in Comparative Example 2 was repeated using Dental Adhesive Composition II-a in combination with OptiBond® All-In-One as follows. After the application of OptiBond® All-In-One adhesive and air-drying, but without light-curing the OptiBond® All-In-One adhesive, one coat of Dental Adhesive Composition II-a was applied to a dentin surface covered with OptiBond® All-In-One adhesive with 20 seconds agitation. The adhesive was then dried with compressed air from a dental air syringe for about five seconds, and polymerized by photo-curing for 20 seconds using an Optilux™ 501 (Kerr Corp.) dental curing light. A plastic mold with an inner diameter of 2.38 mm was securely placed over the adhesive coated dentin surface. The base and catalyst pastes of Nexus® 2 cement were mixed, condensed inside the mold, and allowed to self-cure (or dark-cure) in 37° C. water for 20-24 hours. A bond strength of 30.5±5.8 MPa was obtained, which was a 144% increase over the bond strength obtained in Comparative Example 2. The high bond strength indicated improved compatibility between the inventive Dental Adhesive Composition II-a and self-cured Nexus® 2 resin cement.

Inventive Example 2B

Dental Adhesive Composition II-b
The following were mixed into a homogeneous adhesive composition:

| | |
|---|---|
| 8.37% w/w GDMA-P | (acidic compound) |
| 29.31% w/w Bis-GMA | (non-acidic polymerizable monomer) |
| 12.56% w/w HEMA | (non-acidic polymerizable monomer) |
| 4.19% w/w of ETMPTA | (non-acidic polymerizable monomer) |
| 4.19% w/w GDMA | (non-acidic polymerizable monomer) |
| 25.12% w/w ethanol | |
| 0.84% w/w ODMAB | |
| 0.42% w/w CQ | |
| 0.008% w/w MEHQ | |
| 5.25% w/w ST-OX-50 | |
| 1.00% w/w TS-530, and | |
| 8.75% w/w ST-BAS | |

The ratio of non-acidic polymerizable monomer/acidic compound=50.25%/8.37%=6.0. The Dental Adhesive Composition II-b had a viscosity of 80 cP at 25° C. The Dental Adhesive Composition II-b excluding filler and solvent had an acid number of 0.642 mmol NaOH/gm.

The dentin bond strength test in Comparative Example 2 was repeated using Dental Adhesive Composition II-b in combination with OptiBond® All-In-One as follows. After applying OptiBond® All-In-One adhesive and air-drying, but without light-curing OptiBond® All-In-One adhesive, one coat of Dental Adhesive Composition II-b was applied to a dentin surface covered with OptiBond® All-In-One adhesive with 20 seconds agitation. The adhesive was then dried with compressed air from a dental air syringe for about five seconds, and polymerized by photo-curing for 20 seconds using an Optilux™ 501 (Kerr Corp.) dental curing light. A plastic mold with an inner diameter of 2.38 mm was securely placed over the adhesive coated dentin surface. The base and catalyst pastes of Nexus® 2 cement were mixed, condensed inside the mold, and allowed to self-cure (or dark-cure) in 37° C. water for 20-24 hours. A bond strength of 27.2±5.8 MPa was obtained, which was a 118% increase over the bond strength obtained in Comparative Example 2. The high bond strength indicated improved compatibility between the inventive Dental Adhesive Composition II-b and self-cured Nexus® 2 resin cement.

Comparative Example 3

Adhesion test to a dentin substrate was evaluated using a commercial self-etch priming adhesive Xeno® IV (Dentsply, Pa.) in combination with a commercial resin cement Variolink II (Ivoclar, Vivadent Inc. NY). Bonding strength was evaluated as follows. The dentin surface was polished with wet 600 grit SiC paper. Two coats of Xeno® IV adhesive were applied on the dentin surface and each coat was applied with 20 seconds agitation. The adhesive was then dried with compressed air from a dental air syringe for about five seconds and polymerized by photo-curing for ten seconds using an Optilux™ 501 (Kerr Corp.) dental curing light. A plastic mold with an inner diameter of 2.38 mm was securely placed over the adhesive coated dentin surface. The base and catalyst pastes of Variolink II cement were mixed, condensed inside the mold, and allowed to self-cure (or dark-cure) in 37° C. water for 20-24 hours. The bond strength was tested on an Instron mechanical tester (Model 4467, Instron, MA) using shear force. A bond strength of 7.4±1.5 MPa was obtained. The low bond strength indicated low compatibility between Xeno® IV adhesive and self-cured Variolink II resin cement.

Inventive Example 3

Dental Adhesive Composition III
The following were mixed into a homogeneous adhesive composition:

| | |
|---|---|
| 4.93% w/w GDMA-P | (acidic compound) |
| 39.40% w/w Bis-GMA | (non-acidic polymerizable monomer) |

-continued

| | |
|---|---|
| 14.78% w/w HEMA | (non-acidic polymerizable monomer) |
| 9.85% w/w ETMPTA | (non-acidic polymerizable monomer) |
| 29.55% w/w ethanol | |
| 0.99% w/w ODMAB | |
| 0.49% w/w CQ | |
| 0.01% w/w MEHQ | |

The ratio of non-acidic polymerizable monomer/acidic compound=64.03%/4.93%=13.0. The Dental Adhesive Composition III had a viscosity of 19 cP at 25° C. The Dental Adhesive Composition III excluding filler and solvent had an acid number of 0.386 mmol NaOH/gm.

The dentin bond strength test in Comparative Example 3 was repeated using Dental Adhesive Composition III in combination with Xeno® IV as follows. After applying Xeno® IV adhesive and air-drying, but without light-curing Xeno® IV adhesive, one coat of Dental Adhesive Composition III was applied to a dentin surface covered with Xeno® IV adhesive with 20 seconds agitation. The adhesive was then dried with compressed air from a dental air syringe for about five seconds, and polymerized by photo-curing for 20 seconds using an Optilux™ 501 (Kerr Corp.) dental curing light. A plastic mold with an inner diameter of 2.38 mm was securely placed over the adhesive coated dentin surface. The base and catalyst pastes of Variolink II cement were mixed, condensed inside the mold, and allowed to self-cure (or dark-cure) in 37° C. water for 20-24 hours. The bond strength was tested on an Instron mechanical tester (Model 4467, Instron, MA) using shear force. A bond strength of 28.9±3.0 MPa was obtained, which was a 291% increase over the bond strength obtained in Comparative Example 3. The high bond strength indicated improved compatibility between the inventive Dental Adhesive Composition III and self-cured Variolink II resin cement.

Inventive Example 4

Self-Etch Dental Primer Composition IV-a
The following were mixed into a homogeneous primer composition:

| | |
|---|---|
| 24.87% w/w GDMA-P | (acidic compound) |
| 14.92% w/w HEMA | (non-acidic polymerizable monomer) |
| 4.97% w/w Bis-GMA | (non-acidic polymerizable monomer) |
| 14.92% w/w de-ionized water | |
| 39.79% w/w ethanol | |
| 0.50% w/w CQ | |
| 0.02% w/w MEHQ | |

Dental Adhesive Composition IV-b
The following were mixed into a homogeneous adhesive composition:

| | |
|---|---|
| 4.16% w/w GDMA-P | (acidic compound) |
| 33.30% w/w Bis-GMA | (non-acidic polymerizable monomer) |
| 12.49% w/w HEMA | (non-acidic polymerizable monomer) |
| 8.32% w/w ETMPTA | (non-acidic polymerizable monomer) |
| 24.97% w/w ethanol | |
| 1.25% w/w ODMAB | |
| 0.50% w/w CQ | |
| 0.008% w/w MEHQ | |
| 5.63% w/w ST-OX-50 | |
| 9.38% w/w ST-BAS | |

For the Dental Adhesive Composition IV-b, the ratio of non-acidic polymerizable monomer/acidic compound=54.11%/4.16%=13.0. The Dental Adhesive Composition IV-b had a viscosity of 80 cP at 25° C. The Dental Adhesive Composition IV-b excluding filler and solvent had an acid number of 0.357 mmol NaOH/gm.

Adhesion to each of a human dentin substrate and a bovine enamel substrate was evaluated using Dental Primer Composition IV-a (self-etch primer) and Dental Adhesive Composition IV-b in combination with a light-cure composite resin Herculite XRV (Kerr Corp.). The bond strength was evaluated as follows: Before applying the primer, the human dentin surfaces were polished by 600 grid SiC paper, and the bovine enamel surfaces were cleaned with pumice flour. Dental Adhesive Primer IV-a was applied to each of the human dentin and the bovine enamel with agitation for 20 seconds, and air-dried using compressed air for three to five seconds. A coat of Dental Adhesive Composition IV-b was then applied to each of the primed tooth surfaces and air-dried using compressed air for three to five seconds. The composition was then light-cured for 20 seconds using an Optilux 501 (Kerr Corp.) dental curing light. A plastic mold with an inner diameter of 2.38 mm was securely placed over each of the adhesive-coated tooth surfaces. The composite resin Herculite XRV was condensed inside the mold followed by light curing. After the bonded specimens had been stored in water at 37° C. for about 20-24 hours, dentin and enamel shear bond strengths were measured and were 27.8±7.8 MPa and 30.1±1.7 MPa, respectively. The high enamel bond strength was obtained on un-cut enamel.

To evaluate bond strength to dentin using a self-cured core buildup material, the Dental Primer Composition IV-a (self-etch primer) and Dental Adhesive Composition IV-b were applied to dentin using the same procedures as described in the previous paragraph. Following light-curing of the adhesive, a plastic mold with an inner diameter of 2.38 mm was securely placed over the adhesive coated dentin surface. The base and catalyst pastes of CoreRestore® 2 (Kerr Corp.) core buildup material were mixed, condensed inside the mold, and allowed to self-cure (or dark-cure) in 37° C. water for 20-24 hours. A bond strength of 42.1±9.4 MPa was obtained. The high bond strength indicated excellent compatibility between the inventive Dental Adhesive Composition IV-b and self-cured CoreRestore® 2 core buildup material.

Inventive Example 5

Self-Etch Dental Primer Composition V-a
The following were mixed into a homogeneous primer composition:

| | |
|---|---|
| 22.00% w/w GDMA-P | (acidic compound) |
| 15.00% w/w HEMA | (non-acidic polymerizable monomer) |
| 5.00% w/w Bis-GMA | (non-acidic polymerizable monomer) |
| 12.50% w/w de-ionized water | |
| 44.99% w/w ethanol | |
| 0.50% w/w CQ | |
| 0.02% w/w MEHQ | |

Dental Adhesive Composition V-b
The same components as in Dental Adhesive Composition IV-b in Example 4 were mixed into a homogeneous adhesive composition.

To evaluate the bond strength to dentin using Dental Primer Composition V-a and Dental Adhesive Composition V-b in combination with self-cured resin cements, adhesion to a dentin substrate was evaluated using following procedures: The dentin surface was polished with wet 600 grit SiC paper.

Dental Primer Composition V-a was applied to the dentin with agitation for 20 seconds, and air-dried using compressed air for three to five seconds. A coat of Dental Adhesive Composition V-b was then applied to the primed dentin surface and air-dried using compressed air for three to five seconds. The composition was then light-cured for 20 seconds using an Optilux™ 501 (Kerr Corp.) dental curing light. A plastic mold with an inner diameter of 2.38 mm was securely placed over the adhesive coated tooth surface. The base and catalyst pastes of a resin cement (Nexus® 2 or Maxcem™ (Kerr Corp.)) were mixed, condensed inside the mold, and allowed to self-cure (or dark-cure) in 37° C. water for 20-24 hours. Bond strengths of 34.9±4.5 MPa (with Nexus® 2) and 43.4±5.5 MPa (with Maxcem™) was obtained. The high bond strength indicated excellent compatibility between the inventive Dental Adhesive Composition V-b and self-cured Nexus® 2 or Maxcem™ resin cement.

The adhesive layer had a thickness of about 15 microns according to scanning electron microscopy (SEM) measurement.

Inventive Example 6

Self-Etch Dental Primer Composition VI-a
The following were mixed into a homogeneous primer composition:

| | |
|---|---|
| 24.41% w/w GDMA-P | (acidic compound) |
| 14.65% w/w HEMA | (non-acidic polymerizable monomer) |
| 4.88% w/w Bis-GMA | (non-acidic polymerizable monomer) |
| 14.65% w/w de-ionized water | |
| 41.61% w/w ethanol | |
| 0.39% w/w CQ | |
| 0.02% w/w MEHQ | |

Dental Adhesive Composition VI-b
The following were mixed into a homogeneous adhesive composition:

| | |
|---|---|
| 4.19% w/w GDMA-P | (acidic compound) |
| 33.49% w/w Bis-GMA | (non-acidic polymerizable monomer) |
| 12.56% w/w HEMA | (non-acidic polymerizable monomer) |
| 4.19% w/w ETMPTA | (non-acidic polymerizable monomer) |
| 4.19% w/w GDMA | (non-acidic polymerizable monomer) |
| 25.12% w/w ethanol | |
| 0.84% w/w ODMAB | |
| 0.42% w/w CQ | |
| 0.008% w/w MEHQ | |
| 4.50% w/w ST-OX-50 | |
| 7.50% w/w ST-BAS | |
| 2.00% w/w TS-530 | |
| 1.00% w/w Sodium Hexafluorosilicate | |

For the Dental Adhesive Composition VI-b, the ratio of non-acidic polymerizable monomer/acidic compound=54.43%/4.19%=13.0. The Dental Adhesive Composition VI-b had a viscosity of 80 cP at 25° C. The Dental Adhesive Composition VI-b excluding filler and solvent had an acid number of 0.357 mmol NaOH/gm.

Adhesion to each of a human dentin substrate and a bovine enamel substrates was evaluated using Dental Primer Composition VI-a and Dental Adhesive Composition VI-b in combination with a light-cure composite resin Herculite XRV (Kerr Corp.). The bond strength was evaluated as follows: Before applying primer, the human dentin surfaces were polished by 600 grid SiC paper, and the bovine enamel surfaces were cleaned with pumice flour. Dental Primer Composition VI-a (self-etch primer) was applied to each of the human dentin and the bovine enamel with agitation for 20 seconds, and air-dried using compressed air for three to five seconds. A coat of Dental Adhesive Composition VI-b was then applied to each of the primed tooth surfaces and air-dried using compressed air for three to five seconds. The composition was then light-cured for 20 seconds using an Optilux 501 dental curing light. A plastic mold with an inner diameter of 2.38 mm was securely placed over each of the adhesive coated tooth surfaces. The composite resin Herculite XRV was condensed inside the mold followed by light curing. After the bonded specimens had been stored in water at 37° C. for about 20-24 hours, dentin and enamel shear bond strengths were measured and were 36.8±5.9 MPa and 34.7±2.1 MPa, respectively. Excellent bond strength was obtained on un-cut enamel.

To evaluate the bond strength to dentin using Dental Primer Composition VI-a and Dental Adhesive Composition VI-b in combination with self-cured resin cements, adhesion to a dentin substrate was evaluated using the following procedures: The dentin surface was polished with wet 600 grit SiC paper. Dental Primer Composition VI-a was applied to dentin with agitation for 20 seconds, and air-dried using compressed air for three to five seconds. A coat of Dental Adhesive Composition VI-b was then applied to the primed dentin surface and air-dried using compressed air for three to five seconds. The composition was then light-cured for 20 seconds using an Optilux™ 501 (Kerr Corp.) dental curing light. A plastic mold with an inner diameter of 2.38 mm was securely placed over the adhesive coated tooth surface. The base and catalyst pastes of a resin cement (Nexus® 2 or Maxcem™ (Kerr Corp.)) were mixed, condensed inside the mold, and allowed to self-cure (or dark-cure) in 37° C. water for 20-24 hours. Bond strengths of 30.0±3.1 MPa (with Nexus® 2) and 31.5±5.3 MPa (with Maxcem™) were obtained. The high bond strength indicated excellent compatibility between the inventive Dental Adhesive Composition VI-b and self-cured Nexus® 2 or Maxcem™ resin cement.

Inventive Example 7

Self-Etch Dental Primer Composition VII-a
The following were mixed into a homogeneous primer composition:

| | |
|---|---|
| 21.27% w/w GDMA-P | (acidic compound) |
| 23.21% w/w HEMA | (non-acidic polymerizable monomer) |
| 4.83% w/w Bis-GMA | (non-acidic polymerizable monomer) |
| 14.50% w/w de-ionized water | |
| 35.78% w/w acetone | |
| 0.39% w/w CQ | |
| 0.02% w/w MEHQ | |

Dental Adhesive Composition VII-b
The same components as in Dental Adhesive Composition VI-b as in Example 6 were mixed into a homogeneous adhesive composition.

Adhesion to each of a human dentin and bovine enamel substrates was evaluated using Dental Primer Composition VII-a (self-etch primer) and Dental Adhesive Composition VII-b in combination with a light-cure composite resin Herculite XRV™. The bond strength was evaluated as follows: Before applying the primer, the human dentin surfaces were polished by 600 grid SiC paper, and the bovine enamel surfaces were cleaned with pumice flour. Dental Adhesive Primer VII-a was applied to each of the human dentin and the bovine enamel with agitation for 20 seconds, and air-dried using compressed air for three to five seconds. A coat of Dental Adhesive Composition VII-b was then applied to each of the primed tooth surfaces and air-dried using compressed air for three to five seconds. The composition was then light-cured for 20 seconds using an Optilux 501 dental curing light. A plastic mold with an inner diameter of 2.38 mm was securely placed over each of the adhesive coated tooth surfaces. The composite resin Herculite XRV™ was condensed inside the mold followed by light curing. After the bonded specimens had been stored in water at 37° C. for about 20-24 hours, dentin and enamel shear bond strengths were measured and they were 35.0±5.4 MPa and 33.9±3.3 MPa, respectively. Excellent bond strength was obtained on un-cut enamel.

Other variations or embodiments will also be apparent to one of ordinary skill in the art from the above description and examples. Thus, the forgoing embodiments are not to be construed as limiting the scope of this invention.

What is claimed is:

1. A dental restorative method comprising the steps of:
   (1) applying a dental primer composition comprising at least one first volatile solvent to a tooth structure;
   (2) thereafter applying a dental adhesive composition comprising at least one second volatile solvent to the tooth structure;
   (3) drying the dental adhesive composition to remove the at least one second volatile solvent; and
   (4) hardening the dental adhesive composition by light-curing the dental adhesive composition; wherein the dental primer composition further comprises:
   at least one acidic polymerizable monomer selected from the group consisting of phenyl methacryloxyethyl phosphate, glyceryldimethacrylate phosphate, dipentaerithritol pentaacrylate phosphate, methacryloyloxydecyl phosphate, and hydroxyethylmethacrylate phosphate; and
   wherein the dental adhesive composition further comprises:
   (i) at least one non-acidic polymerizable monomer having at least one ethylenically unsaturated group;
   (ii) at least one acidic compound having at least one ethylenically unsaturated group and at least one acidic moiety selected from the group consisting of carboxylic acid, carboxylic acid anhydride, phosphonic acid or its salt or ester derivatives, phosphoric acid or its salt or ester derivatives, and combinations thereof,
   (iii) at least one photoinitiator, and
   (iv) about 0-40% by weight of one or more fillers;
   wherein when the adhesive composition comprises at least one acidic compound the weight ratio of non-acidic polymerizable monomers/acidic compounds in the dental adhesive composition is more than 4.5; the viscosity of the dental adhesive composition is less than 350 centipoise (cP) at 25° C.; and the dental adhesive composition excluding solvent and filler has an acid number of less than 0.75 mmol NaOH/g; and wherein the hardened dental adhesive has a film thickness less than 30 microns.

2. The method of claim 1, wherein the weight ratio of non-acidic polymerizable monomers/acidic compounds in the dental adhesive composition is more than 8.

3. The method of claim 1, wherein the dental adhesive composition excluding solvent and filler has an acid number less than 0.5 mmol NaOH/g.

4. The method of claim 1, wherein the viscosity of the dental adhesive composition is less than 150 cP at 25° C.

5. The method of claim 1, wherein the ethylenically unsaturated group of the at least one non-acidic polymerizable monomer is selected from the group consisting of vinyl, acrylate, methacrylate, acrylamide, methacrylamide, and combinations thereof.

6. The method of claim 1, wherein the at least one non-acidic polymerizable monomer in the dental adhesive composition has at least one hydroxyl group.

7. The method of claim 1, wherein the at least one first volatile solvent and the at least one second solvent are independently selected from the group consisting of ethanol, water, methanol, acetone, methyl ethyl ketone, isopropanol, t-butanol, and combinations thereof.

8. The method of claim 1, wherein the at least one first volatile solvent in the dental primer composition is selected from the group consisting of water, ethanol, methanol, acetone, methyl ethyl ketone, isopropanol, t-butanol, and combinations thereof.

9. The method of claim 1, wherein the at least one second volatile solvent in the dental adhesive composition is selected from the group consisting of ethanol, methanol, acetone, methyl ethyl ketone, isopropanol, t-butanol, and combinations thereof.

10. The method of claim 1, wherein the concentration of at least one second volatile solvent in the dental adhesive composition is in the range of about 15% w/w to about 60% by weight of the dental adhesive composition.

11. The method of claim 1, further comprising:
    (5) drying the dental primer composition to remove the at least one first volatile solvent prior to step (2).

12. The method of claim 1, wherein the dental primer composition further comprises one or more components selected from the group consisting of a non-acidic polymerizable monomer having at least one ethylenically unsaturated group, a polymerization initiator, a filler, a stabilizer, a fluoride-releasing compound, an antimicrobial additive, and combinations thereof.

13. The method of claim 1, wherein the dental primer composition comprises about 1% w/w to about 50% w/w of the at least one acidic polymerizable monomer; about 0-60% w/w of one or more non-acidic polymerizable monomer; about 1% w/w to about 50% w/w water; about 0-70% w/w of one or more organic solvents selected from the group consisting of ethanol, acetone, methyl ethyl ketone, isopropanol, t-butanol, and combinations thereof; and optionally at least one component selected from the group consisting of a polymerization initiator, a filler, a stabilizer, a fluoride-releasing compound, an antimicrobial additive, and combinations thereof.

14. The method of claim 1, wherein the dental primer composition comprises about 5% w/w to about 35% w/w of the at least one acidic polymerizable monomer; about 1% w/w to about 40% w/w of at least one non-acidic polymerizable monomer; about 5% w/w to about 35% w/w of water; about 10% w/w to about 60% w/w of at least one organic solvent selected from the group consisting of ethanol, acetone, methyl ethyl ketone, isopropanol, t-butanol, and combinations thereof; and optionally one or more components selected from the group consisting of a polymerization initiator, a filler, a stabilizer, a fluoride-releasing compound, an antimicrobial additive, and combinations thereof.

15. The method of claim 1, wherein the hardened dental adhesive has a film thickness of about 15 microns.

16. The method of claim 1, further comprising the steps of preparing the tooth structure and optionally etching the tooth structure with an acidic etchant prior to applying the dental primer composition.

17. The method of claim 1, further comprising the steps of applying a composite resin or a pit/fissure sealant to the tooth structure after (4), and hardening the composite resin or pit/fissure sealant by a method selected from the group consisting of light-curing, self-curing, and dual-curing.

18. The method of claim 1, further comprising the steps of attaching a prosthetic or orthodontic device to the tooth structure after (4) with a resin cement and hardening the resin cement by a method selected from the group consisting of light-curing, self-curing, and dual-curing.

19. The method of claim 1, wherein the weight ratio of non-acidic polymerizable monomers/acidic compounds in the dental adhesive composition is more than 6.

20. The method of claim 1, wherein the weight ratio of non-acidic polymerizable monomers/acidic compounds in the dental adhesive composition is more than 10.

\* \* \* \* \*